United States Patent
Esswein et al.

(10) Patent No.: US 6,818,623 B2
(45) Date of Patent: Nov. 16, 2004

(54) ACTIVE HEDGEHOG PROTEIN CONJUGATE

(75) Inventors: Angelika Esswein, Buettelborn (DE); Kurt Lang, Penzberg (DE); Petra Rueger, Penzberg (DE); Tilman Seytter, Graefelfing (DE)

(73) Assignee: Curis, Inc., Cambridge, MA (US)

( * ) Notice: Subject to any disclaimer, the term of this patent is extended or adjusted under 35 U.S.C. 154(b) by 4 days.

(21) Appl. No.: 10/278,060

(22) Filed: Oct. 21, 2002

(65) Prior Publication Data

US 2003/0139574 A1 Jul. 24, 2003

Related U.S. Application Data

(63) Continuation of application No. 09/301,199, filed on Apr. 28, 1999, now Pat. No. 6,468,978.

(30) Foreign Application Priority Data

Apr. 30, 1998 (EP) .............................................. 98107911
Sep. 3, 1998 (EP) ............................................. 98116733

(51) Int. Cl.[7] ........................ A61K 38/17; C07K 1/113; C07K 14/47
(52) U.S. Cl. ........................... 514/21; 514/12; 530/350; 530/408; 530/409; 530/410
(58) Field of Search .................................. 530/350, 395, 530/402, 403, 404, 405, 406, 408, 409, 410; 514/2, 8, 12, 21; 424/94.3, 94.63; 435/188, 212, 219, 226

(56) References Cited

U.S. PATENT DOCUMENTS 5,844,079 A 12/1998 Ingham et al. ............... 530/350
6,444,793 B1 * 9/2002 Pepinsky et al. ............ 530/402
6,468,978 B1 * 10/2002 Esswein et al. ................ 514/21

FOREIGN PATENT DOCUMENTS

| WO | WO 95/18856 | 7/1995 |
| WO | WO 98/02454 | 1/1998 |
| WO | WO 98/30576 | 7/1998 |

OTHER PUBLICATIONS

Farese, R.V. et al. Trends in Genetics 14, 115–120 (Mar. 1998).
Hammerschmidt et al. Trends in Genetics 13, 14–21 (Jan. 1997).
Hancock, J.F. et al. Cell 63, 133–139 (Oct. 1990).
Hynes, M. et al. Neuron 15, 35–44 (Jul. 1995).
Mohler, J. et al. Development 115, 957–971 (1992).
Nakamura, T. et al. Biochem. Biophys. Res. Comm. 237, 465–469 (1997).
Pepinsky, R.B. et al. J. Biol. Chem. 273, 14037–14045 (May 1998).
Porter, J.A. et al. Cell 86, 21–34 (Jul. 1996).
Porter, J.A. et al. Science 274, 255–259 (Oct. 1996).
Seytter, T. et al. Bone 23, Abstract SA151 (Nov. 1998).

* cited by examiner

Primary Examiner—Jeffrey Edwin Russel
(74) Attorney, Agent, or Firm—Ropes & Gray LLP

(57) ABSTRACT

A hedgehog conjugate which is characterized in that it contains: a) a polypeptide composed of 10 to 30 hydrophobic amino acids and/or amino acids which form transmembrane helices and are positively charged, b) 1 to 4 aliphatic, saturated or unsaturated hydrocarbon residues with a chain length of 10 to 24 C atoms and with a hydrophobic action or c) a hydrophobic thio compound covalently bound to a hedgehog protein and which has a several-fold increased activity and is suitable as a pharmaceutical agent.

14 Claims, 2 Drawing Sheets

SEQUENCE LISTING

<160> NUMBER OF SEQ ID NOS: 5

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: Primer 344

<400> SEQUENCE: 1

-continued

```
cagaattctt gcggaccggg cagggg                                              26

<210> SEQ ID NO 2
<211> LENGTH: 36
<212> TYPE: DNA
<213> ORGANISM: Artificial Sequence
<220> FEATURE:
<223> OTHER INFORMATION: Description of Artificial Sequence: Primer 345

<400> SEQUENCE: 2
gactgcagtt aatcattagc ctcccgattt ggccgc                                   36

<210> SEQ ID NO 3
<211> LENGTH: 45
<212> TYPE: DNA
<213> ORGANISM: Artificial Sequence
<220> FEATURE:
<223> OTHER INFORMATION: Description of Artificial Sequence: Primer 346

<400> SEQUENCE: 3
aattcatgca tcatcaccac caccacgatg acgacgacaa atgcg                         45

<210> SEQ ID NO 4
<211> LENGTH: 44
<212> TYPE: DNA
<213> ORGANISM: Artificial Sequence
<220> FEATURE:
<223> OTHER INFORMATION: Description of Artificial Sequence: Primer 347

<400> SEQUENCE: 4
gtccgcattt gtcgtcgtca tcgtggtggt ggtgatgatg catg                          44

<210> SEQ ID NO 5
<211> LENGTH: 89
<212> TYPE: DNA
<213> ORGANISM: Artificial Sequence
<220> FEATURE:
<223> OTHER INFORMATION: Description of Artificial Sequence: Adapter
      346/347

<400> SEQUENCE: 5
aattcatgca tcatcaccac caccacgatg acgacgacaa atgcggtacg tagtagtggt         60
ggtggtgcta ctgctgctgt ttacgcctg                                           89
```

ACTIVE HEDGEHOG PROTEIN CONJUGATE

This application is a continuation of U.S. application Ser. No. 09/301,199, now U.S. Pat. No. 6,468,978, filed Apr. 28, 1999.

The invention concerns a hedgehog protein conjugate with increased activity, a process for its production and its therapeutic use.

BACKGROUND OF THE INVENTION

Hedgehog (hh) proteins are understood as a family of secreted signal proteins which are responsible for the formation of numerous structures in embryogenesis (J. C. Smith, Cell 76 (1994) 193–196, N. Pemmon, Cell 80 (1995) 517–520, C. Chiang et al., Nature 83 (1996) 407, M. J. Bitgood et al., Curr. Biol. 6 (1996) 296, A. Vortkamp et al., Science 273 (1996) 613, C. J. Lai et al., Development 121 (1995) 2349). During its biosynthesis a 20 kD N-terminal domain and a 25 kD C-terminal domain are obtained after cleavage of the signal sequence and autocatalytic cleavage. In the naturally occurring protein the N-terminal domain is modified with cholesterol at its C-terminus after cleavage of the C-terminal domain (J. A. Porter et al., Science 274 (1996) 255–259). In higher life-forms the hh family is composed of at least three members namely sonic, indian and desert hh (shh, Ihh, Dhh; M. Fietz et al., Development (Suppl.) (1994) 43–51). Differences in the activity of hedgehog proteins that were produced recombinantly were observed after production in prokaryotes and eukaryotes (M. Hynes et al., Neuron 15 (1995) 35–44 and T. Nakamum et al., Biochem. Biophys. Res. Comm. 237 (1997) 465–469).

Hynes et al. compare the activity of hh in the supernatant of transformed human embryonic kidney 293 cells (eukaryotic hh) with hh produced from E. coli and find a four-fold higher activity of hh from the supernatants of the kidney cell line. The reason for this increased activity of hh has been discussed to be a potential additional accessory factor which is only expressed in eukaryotic cells, a posttranslational modification, a different N-terminus since the hh isolated from E. coli contains 50% of a hh form which carries two additional N-terminal amino acids (Gly-Ser) or is shortened by 5–6 amino acids, or a higher state of aggregation (e.g. by binding to nickel agarose beads).

Nakamura et al. compare the activity of shh in the supernatant of transformed chicken embryo fibroblasts with an shh fusion protein isolated from E. coli which still has an N-terminal polyhistidine part. The shh in the supernatant of the fibroblasts has a seven-fold higher activity than the purified E. coli protein with regard to stimulation of alkaline phosphatase (AP) in C3H10T ½ cells. The increased activity has been postulated to be due to synergism of hh with molecules such as bone morphogenetic proteins (BMPS) which are only present in the supernatant of eukaryotic cells and in combination with hh cause the stronger induction of AP.

Kinto et al., FEBS Letters, 404 (1997) 319–323 describe that fibroblasts which secrete hh induce ectopic bone formation in an i.m. implantation on collagen. However, such an activity is not known for an isolated hh protein.

SUMMARY OF THE INVENTION

This invention provides a hedgehog conjugate, comprising from 1 to 4 moieties covalently bound to a hedgehog protein; wherein each moiety is: a) a polypeptide composed of 10 to 30 hydrophobic amino acids and/or amino acids which form transmembrane helices and are positively charged, b) an aliphatic, saturated or unsaturated hydrocarbon residue with a chain length of 8 to 24 C atoms and with a hydrophobic action, or c) a hydrophobic thio group.

The object of the invention is to provide hh protein (polypeptide) conjugates which have a considerably improved activity compared to the known forms. The conjugates of this invention have the same utility as the corresponding unconjugated hedgehog protein.

DETAILED DESCRIPTION OF THE INVENTION

Figure 1:
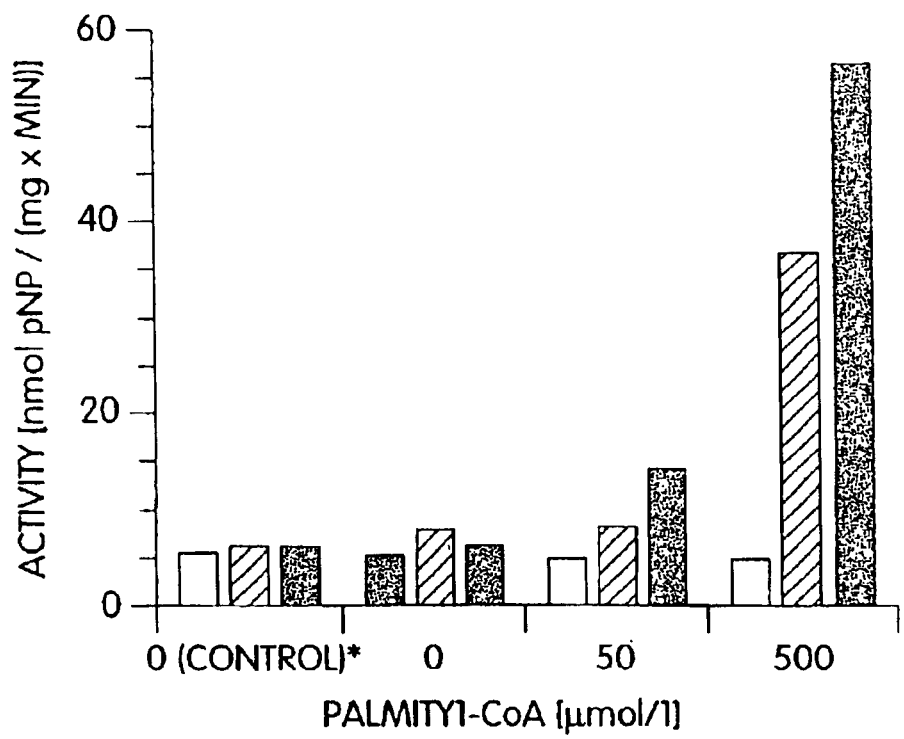
FIG. 1: shows the activity of recombinant human shh after derivatization with palmitoyl-CoA.

This invention provides a hedgehog protein produced recombinantly that has artificially been made lipophilic. Such a lipophilization is preferably achieved by chemical modification. Such a hedgehog conjugate preferably contains an additional polypeptide that is covalently bound (preferably at the C-terminus or/and N-terminus) and is composed of 10–30 preferably hydrophobic amino acids and/or those amino acids which form transmembrane helices. The additional polypeptide particularly preferably contains 2–12 lysines and/or arginines but no polyhistidine part that would be suitable for purifying the conjugate on a Ni chelate column. It is also preferable to covalently bind (preferably at the C-terminus and/or N-terminus) 1–4 aliphatic, saturated or unsaturated hydrocarbon residues with a chain length of 8–24 C atoms or steroids with a lipophilic (hydrophobic) action. Furthermore it is preferred to covalently couple hydrophobic thio compounds, such as in particular thiocholesterol and thioalkanes, thioalkenes, to hh proteins via a disulfide bridge formed oxidatively (preferably at the C-terminus and/or N-terminus and in this case on the N-terminal cysteine).

The protein is hydrophobized by such lipophilizing residues which improves its interaction with lipid membranes of eukaryotic cells, in particular of mammalian cells.

Consequently a lipophilized protein according to the invention is understood as a hydrophobized protein which has an increased surface hydrophobicity compared to an unmodified protein which increases its affinity for apolar molecules or amphiphiles.

The increase in the degree of lipophilicity of the protein can be measured by the degree of integration in a lipid layer as described for example by Haque, Z. et al., J.Agric.Food Chem. 30 (1982), 481. Methods for the hydrophobic (lipophilizing) modification of proteins are for example described by Haque, Z. et al., J.Agric.Food Chem. 31 (1983) 1225–1230; Webb, R. J. et al., Biochemistry 37 (1998) 673–679; Hancock, J. F., Cell 63 (1990) 133–139; A Practical guide to membrane protein purification, Ed. G. v. Jagow, Hermann Schägger (1994), (chapter 16, pages 535–554).

It has surprisingly turned out that such lipophilized hedgehog proteins (also denoted hedgehog conjugates (hh conjugates) in the following) exhibit a drastically increased activity of preferably at least 10-fold, particularly preferably of $10^3$–$10^5$-fold compared to non-modified hedgehog proteins (e.g. after cytoplasmic expression in E. coli) especially in a pharmaceutical formulation and in vitro. In addition it is particularly surprising that such hedgehog conjugates according to the invention can be used particularly advantageously for a local therapy preferably on bones, on cartilage, on nerve cells (in nerve lesions or neurodegenerative diseases) or in muscle tissue.

It is known from Yang et al., Development 124 (1997) 4393–4404 that high local hedgehog concentrations must prevail over a period of at least 16 h at the site of action in the body for a pharmaceutically effective in vivo activity. The carrier system for this described by Yang et al. i.e. the hedgehog-loaded chromatography medium affigel CM, the Ni agarose described by Marti et al., in Nature 375 (1995) 322–325 or the Affigel blue used by Lopez-Martinez at al., in Curr.Biol. 5 (1995) 791–796 or the heparin agarose particles that they used are less suitable for a pharmaceutical application since they are immunogenic and can cause inflammatory reactions.

The conjugates according to the invention serve as new active substances for the production of pharmaceutical forms of administration. Overall the coupling results in an improved pharmacokinetic profile of the hedgehog protein. The hydrophobic hydrocarbon residue results in a localization of the hedgehog protein on the membrane of the target cells which, in addition to facilitating integration into the cell interior, above all results in a substantially more prolonged presence on the cell surface which is optimal for the pharmacological effect.

The conjugates according to the invention do not necessarily need to be additionally coupled to a carrier for slow release. The hedgehog conjugates according to the invention are also highly active at the site of action in the body without a delayed release occurring from a carrier over a long period (several days). Nevertheless it is expedient to use a pharmaceutical composition for the local application of the hedgehog conjugates according to the invention which contains the conjugate according to the invention together with a carrier matrix. The carrier matrix essentially serves to facilitate the local application in particular by providing such a pharmaceutical composition with a suitable minimum viscosity for the local application. The pharmaceutical composition is preferably buffered in the pH range between pH 4 and 9 and contains one or several non-ionic detergents such as polyoxysorbate or polyoxyethylene type detergents (e.g. Tween®20, Tween®80, Triton®X-100), octylglucoside or ionic detergents such as sodium deoxycholate, sodium cholate, sodium taurodeoxycholate.

In a preferred embodiment a hh protein is expressed which contains an additional 10–30 mainly hydrophobic amino acids at the N-terminus and/or C-terminus since these are also incorporated into the membrane of cells [Webb et al., Biochemistry 37 (1998) 673–679, Skolnick et al., Biol. Membranes (1996) 536–554; ed.: Merz and Roux]. Hydrophobic amino acids within the sense of the invention are understood as amino acids which have a negative free energy in the transition from the aqueous phase into a hydrophobic/organic phase. Furthermore N-terminal and/or C-terminal sequences which are known to form transmembrane helices such as e.g. the M28 peptide or which interact as a helix with the surface of membranes such as e.g. maginin 2 (Skolnick et al., 1996) are also suitable for increasing the activity of hh proteins.

In a further preferred embodiment the N-terminus and/or C-terminus of the hedgehog protein is modified by a polypeptide residue which contains 2–12 lysines and/or arginines. In this case it is possible to omit the modification with the hydrocarbon residue.

An aliphatic, saturated or unsaturated hydrocarbon residue with a hydrophobic action and a chain length of 8–24, preferably 10–24, most preferably. 12–18 C atoms, is preferably a saturated or monounsaturated to polyunsaturated fatty acid or alkyl alcohol residue optionally interrupted by an oxygen or sulphur atom or a carbonyl group. Particularly preferred saturated fatty acids are: capric acid, lauric acid, myristic acid, palmitic acid, stearic acid, arachidic acid and behenic acid. Preferred mono-unsaturated fatty acids are myristic acid, palmitoleic acid and oleic acid. Particularly preferred polyunsaturated fatty acids are linoleic acid, linolenic acid and arachidonic acid. Such fatty acid residues are preferably coupled via an ester, acid amide, disulfide or thioester bond to reactive groups of the protein.

The number of hydrophobic hydrocarbon chains per protein molecule can be suitably controlled by the reaction conditions (e.g. dilution) or by the selection of the amino acid to be modified. For example shh contains three cysteines of which the N-terminal cysteine is particularly reactive. In this case the reaction procedure can lead to the N-terminal cysteine being modified with either one or more hydrophobic hydrocarbon chains. It is also possible to statistically modify two or almost all three cysteines. Although when modifying other amino acids it is preferable to modify defined amino acids, it is also possible to use derivatized hedgehog proteins for the pharmaceutical composition in which there is a statistical distribution of hydrocarbon chain modifications of ca. 1 to ca. 4 chains per molecule. Although a higher number of hydrocarbon chains per molecule is suitable, the solubility in a pharmaceutical composition is decreased by this and it can lead to disturbances in the active three dimensional protein structure. When coupling with long chain alkyl groups ($C_{14}$–$C_{24}$, preferably $C_{16}$–$C_{24}$) it is preferable to only link 1–2 carbon chains and when short-chain carbon chains are coupled, it is, however, preferable to couple 2–3 alkyl groups.

In a preferred embodiment the derivatization can also comprise the coupling of two hydrophobic hydrocarbon chains to one amino acid. This can for example be achieved by coupling a fatty acid diglyceride to the amino acid.

As hedgehog proteins are very unstable, in a preferred embodiment a hedgehog protein is used for the coupling in which the SH group of the N-terminal cysteine is protected. An SH coupling product is then obtained by reduction of the protected SH groups immediately before or during the coupling procedure. It is preferable to protect the SH group of said cysteine by forming a homologous hedgehog disulfide or a mixed disulfide (e.g. with GSH or β-mercaptoethanol).

Thiol-protecting groups are known in the art, including, but not limited to, the triphenylmethyl (trityl) and s-t-butyl, s-p-nitrobenzyl and s-p-methoxy-benzyl (see, e.g., Greene and Wuts, Protective Groups in Organic Synthesis, second edition, John Wiley & Sons, New York (1991), and Atherton et al., The Peptides, Gross and Meienhofer, eds., Academic Press, New York (1983), Vol. 19, 1–38). Such thiol-protected or homo-dimerized hedgehog proteins are valuable intermediates for the production of SH-modified hedgehog proteins and are subject-matters of the present invention.

The invention further relates to the use of hedgehog proteins, in which the SH group of the N-terminal cysteine is protected or homo-dimerized as stable intermediates, for the production of SH-modified hedgehog proteins. In this process, the protective group is cleaved off or the homologous dimer is cleaved and reacted with the activated derivatization reagent.

The following methods are preferred for coupling SH-protected hedgehog proteins:

I. Reduction of the disulfide or cleavage of the protecting group in the coupling mixture preferably when the coupling occurs via imidazolides or CoA derivatives.

II. Reduction of the disulfide, isolation of the unprotected monomers in an acidic medium and immediate coupling in a neutral range using an activated disulfide (e.g. pyridyl-SS) as a coupling reagent.

It has turned out that a double acylation on the N-terminal cysteine mainly occurs in the coupling via imidazolide or CoA derivatives (ca. 60–70%) in which case the coupled hydrophobic compound is present in the one case bound as an acid amide and in the other case it is bound as a thioester. Selective cleavage of the hydrophobic compound bound as a thioester enables the synthesis of a mono-hydrophobized hedgehog protein. Such a selective cleavage is carried out with a reducing agent such as DTE or hydroxylamine.

Coupling via an activated disulfide such as for example pyridyl-SS derivatives leads to a monoalkylation. The described process according to the invention enables numerous hydrophobic substances such as steroids, carbon chains (e.g. fatty acids) containing thiol groups to be coupled to hedgehog proteins.

Consequently a further subject-matter of the invention is a process for the production of an SH-modified hedgehog protein or of an N-terminal fragment thereof, preferably a fragment essentially containing the N-terminal domain which is characterized in that the thiol group of the N-terminal cysteine of the hedgehog protein is protected, the protein modified in this manner is isolated and, after cleavage of the protecting group, the hedgehog protein is derivatized at the N-terminal cysteine, preferably by covalent coupling of a hydrophobic compound such as a fatty acid or a steroid to the SH group. Such a coupling is preferably reversible and can be reversed by the physiological reducing conditions present in a mammalian cell and in vivo resulting in the formation of a non-hydrophobized hedgehog protein.

A further subject-matter of the invention is a process for coupling hydrophobic compounds to hedgehog proteins or fragments thereof via the SH group of the N-terminal cysteine which is characterized in that the thiol group of the N-terminal cysteine of the hedgehog protein is protected, said protected SH group is reduced and said hedgehog protein is reacted with an activated derivative of the hydrophobic compound to form a thiol bond between the hedgehog protein and hydrophobic compound. In a preferred embodiment an additional molecule of the hydrophobic compound can be coupled to the hedgehog protein by means of an amide bond.

Imidazolide and CoA derivatives of hydrophobic compounds are for example suitable as activated hydrophobic compounds. Such activated compounds are preferably used in method I (see supra).

Pyridyl disulfide derivatives of hydrophobic compounds are also suitable as activated hydrophobic compounds. Such activated compounds are preferably used in method (see supra).

Natural or unnatural saturated and monounsaturated or polyunsaturated fatty acids and in particular saturated fatty acids with a chain length of 4–18, preferably 8–18 C atoms or steroids are preferably used to acylate hedgehog proteins by the imidazolide process, whereby conjugates are obtained in which the hydrocarbon residues have a chain length of 8–24 C atoms.

In order to link hydrophobic compounds with hedgehog proteins by the pyridyl disulfide process it is preferable to use natural or unnatural saturated and monounsaburated or polyunsaturated mercaptoalkanes and in particular saturated carbon chains containing a thiol group with a chain length of 8–24 C atoms, mercapto-steroids and in particular thiocholesterol.

In the process according to the invention it is preferable to use the hedgehog protein at a concentration of 0.01–10 mg/ml, particularly preferably of 3 mg/ml. The salt concentration is preferably 0–2 mol/l. Sodium chloride is preferably used. The molar ratio of the coupling reagent to the protein is advantageously 1:2 to 20:1. Preferred buffers are: Hepes buffer, phosphate buffer and MES buffer. The coupling reactions are preferably carried out in the pH range between 4.5 and 8.5, preferably at pH 6.5–7.5. The reaction time depends on the conditions used and is expediently 5 minutes to 5 days for the preparation of dipalmitoylated shh. The reaction is preferably carried out in a temperature range between 0–40° C. The proportion of by-products is low at low temperatures, preferably at temperatures below 10° C., e.g. 4° C.

The addition of detergents is particularly advantageous for the process according to the invention. Such reagents can for example be ionic or non-ionic detergents. Zwitterionic detergents are preferred. Preferred concentrations are about 0.5–3% (v/v).

The hydrocarbon chain or the hydrocarbon chains or steroids are expediently coupled to reactive groups of the protein for example to free hydroxy, mercapto, carboxy or amino groups via an amide bond, an ester, disulfide or thioester bond. Such processes are known to a person skilled in the art and are described for example in Wong, S. S., Chemistry of Protein Conjugation and Cross Linking, CRC Press, Boca Raton, Fla., USA, 1993. For example fatty acids can be coupled as thioesters with coenzyme A (e.g. palmitoyl coenzyme A) via a succinimide ester or N-maleimide coupling (e.g. palmitic acid N-hydroxy succinimide ester) via a fatty acid anhydride, fatty acid imidazolide or acid chloride.

Coupling processes for palmitoyl-CoA, stearoyl-CoA or myristoyl-CoA are for example described by Ross et al., J. Neurosci. Res. 21 (1988) 35–44, Bizzozero et al., J. Biol.Chem. 262 (1987) 2138–2145 or for tubulin by Ozols, J. et al., Molec.Biol. of the Cell 8 (1997) 637–645. A derivatization with fatty acid anhydrides has for example been described for ovalbumin (Segawa, A., et al., Int.Archs Allergy appl. Immun. 66 (1981) 189–199) or for peptides (Yadav, S. P. et al., Biochem.Biophys.Res. Comm. 205 (1994) 1688–1695). Numerous examples also exist for an acylation with fatty acid succinimide esters e.g. for casein (Haque, Z. et al., J. Agric.Food Chem. 31 (1983) 1225–1230), (Haque, Z. et al., Agric.Biol.Chem. 46 (1982) 597–599). An N-terminal coupling to cysteine can also occur via an aldehyde group on the fusion partner (e.g. palmitoyl-Cys-CHO) (Liu et al., Proc.Natl.Acad.Sci. USA 91 (1994) 6584–6588). N-terminal coupling to serine can be achieved by conversion into an aldehyde group, reaction with hydrazide (e.g. palmitoyl-Cys hydrazide) and stabilization of the hydrazone that is formed (e.g. by reduction with $NaBH_3CN$) (Gaertner et al., Bioconjugate Chem. 3 (1992) 262–268).

The hydrophobic hydrocarbon chain is bound depending on the coupling chemistry for example in the form of an ether, thioether, ester, thioester, disulfide or amide to the side groups of the reactive amino acids serine, threonine, glutamic acid, aspartic acid, cysteine, arginine or lysine. Methods for specific coupling to particular amino acids are described by Wong, S. S., in Chemistry of Protein Conjugation and Cross Linking, CRC Press Inc., Boca Raton, Fla., USA (1993) and Lundblad in Techniques in Protein Modification (1995).

In a preferred embodiment of the invention, the hydrophobic compounds are solubilized in an organic solvent or mixture of an organic solvent and water preferably containing more than 10% (v/v) organic solvent. Such organic solvents are preferably dioxane, tetrahydrofurane or isopropanol. For coupling of the hydrophobic compound and the hedgehog protein such solutions of the hydrophobic compounds are combined with a detergent-containing solution of the hedgehog protein, preferably in its protected form, in such a way that the mixture contains 10% or less of organic solvent. It was found that hedgehog protein solutions containing more than 10% of organic solvent lead to the precipitation and/or denaturation of the hedgehog protein.

In a further preferred embodiment, thiocholesterol is coupled to the thiol group in particular of the N-terminal cysteine by means of an oxidatively formed disulfide bridge in the presence of solubilizing detergents such as in particular sodium deoxycholate, sodium cholate, sodium taurodeoxycholate, octyl glucoside or Triton® X-100. In contrast to the N-terminal hh fragment which is modified naturally on the C-terminus by cholesterol, a hh form is produced in this process which contains a thiocholesterol at the N-terminus. This form has a similarly increased activity to the natural form but can be produced much more simply and in larger amounts. Due to the cytoplasmic lability of disulfide bridges this hh form has no or only a slight immunogenic potential.

In order to increase the solubility of lipophilically modified hh proteins it is additionally preferable to carry out the derivatization and/or subsequent purification or pharmaceutical formulation in the presence of soluble, anionic polysaccharides such as suramin and heparin.

Activity within the sense of the invention is understood as the activity of alkaline phosphatase which the polypeptide can induce in mammalian cells (activity in the alkaline phosphatase test). In this method a mouse fibroblast cell line is cultured in a medium which contains foetal calf serum. Subsequently sterile filtered sample is added, the cells are lysed after ca. 5 days and alkaline phosphatase is determined in the cell lysate by means of the cleavage of a chromogenic substrate (pNP, p-nitrophenol) (J. Asahina, Exp. Cell. Res. 222 (1996) 38–47 and T. Nakamura (1997)).

A hedgehog protein according to the invention is understood as a secreted signal protein (19 kD N-terminal signalling domain) which is responsible for the formation of numerous structures in embryogenesis. Sonic, indian or desert hh are particularly preferably used (Fiete M. et al., Development (Suppl.) (1994) 43–51). A hh protein with a sequence as described in the EMBL databank under the No. L38518 is preferably used. Proteins of the hedgehog family exhibit a pronounced homology in their amino acid sequence which is why it is also preferable to express those nucleic acids which code for hedgehog proteins which are 80% or more homologous with the abovementioned sequence of sonic hedgehog protein (shh). Protein homology can be determined with the aid of the computer programs Gap or BestFit (University of Wisconsin; Needleman and Wunsch, J. Mol. Biol. 48 (1970) 443–453; Smith and Waterman, Adv. Appl. Math. 2 (1981) 482–489).

The human sonic hedgehog precursor protein is composed of the amino acids 1–462 of the sequence described in the EMBL databank under No. L38518. The amino acids 1–23 represent the signal peptide, the amino acids 24–197 represent the mature signal domain, the amino acids 32–197 represent the signal domain shortened by eight amino acids and the amino acids 198–462 represent the autoprocessing C-terminal domain after autoproteolytic cleavage. Accordingly the N-terminus or C-terminus of the hh protein where the coupling preferably takes place is understood according to the invention as the first amino acids (N-terminus) or the last amino acids (C-terminus) of the N-terminal signalling domains 24–197. It is preferable to couple to one or several amino acids of the first or last 10 amino acids. It is particularly preferable to couple to the first or second amino acid of the N-terminus of the N-terminal domain (AA 24 or 25) or the last or next to last amino acid of the C-terminus of the N-terminal domain (AA 196 or 197). In the hedgehog conjugates according to the invention lipophilic groups or hydrocarbon chain(s) are preferably coupled to the N-terminal domain of a hh protein and the coupling product is in particular a thioester or amide of the N-terminal cysteine at position 24 with lauric, myristic, palmitic, palmitoleic, stearic or oleic acid or a steroid or it is a hh protein to which a thiocholesterol or mercaptoalkane/-alkene is bound via a disulfide bridge. The production of unmodified hh protein is preferably carried out recombinantly using methods familiar to a person skilled in the art, preferably in a prokaryotic (e.g. E. coli) expression system. The hedgehog protein is preferably produced recombinantly as a fusion protein in a soluble manner, isolated from the supernatant of the cell culture or, after lysis of the host cells, the (preferably N-terminal) fusion part (e.g. polyHis, streptavidine, etc.) is cleaved by a sequence-specific protease such as enterokinase, and the free thiol group of the N-terminal cysteine is protected either by reaction with a thiol-protecting reagent or by dimerization of the hedgehog protein via disulfide bridging at said cysteine.

The pharmaceutical composition according to the invention contains a pharmacologically effective dose of the hh conjugate and can be administered preferably locally. It is preferable to use the conjugates according to the invention in combination with other proteins of the hedgehog family or bone growth factors such as bone morphogenetic proteins (BMPs) (Wozney et al., Cell.Mol.Biol. of Bone, Bone Morphogenetic Proteins and their Gene Expression (1993) Academic Press Inc., 131–167) or parathyroid hormones (Karablis et al., Genes and Development 8 (1994) 277–289) or insulin-like growth factors (IGF-1 or 11) or transforming growth factors (TGF-β).

In a further preferred embodiment a pharmaceutical composition of the hedgehog conjugate according to the invention containing suramin is preferred and this can be advantageously used.

In a preferred embodiment the pharmaceutical composition contains the hedgehog conjugate at a concentration of 0.01–10 mg/ml, in particular 0.01 to 1 mg/ml.

In a preferred embodiment the pharmaceutical composition additionally contains a pharmaceutically acceptable buffer which is biocompatible preferably in a range between pH 4 and pH 10, particularly preferably in a range between pH 6 and 9, in particular at a pH value of ca. pH 7. The pH value of the pharmaceutical composition should be expediently higher than pH 4 in order to prevent denaturation of the folded structure and detachment of the zinc complexed in the hedgehog protein. The concentration of the buffer is preferably 1–500 mmol/l, preferably 10–100 mmol/l. Hence in a suitable embodiment 20 mmol/l potassium phosphate buffer pH 7.2 is used as the buffer.

Furthermore it is preferable for the production of the pharmaceutical composition to add auxiliary substances such as a sugar (mannitol; sucrose, lactose, glucose, sucrose, trehalose, preferably 20–100 mg/ml) or an amino acid such as glycine or arginine as well as antioxidants such as EDTA, cirate, polyethylene glycol (1–10% by weight), ascorbic acid, tocophenol, detergents, preferably non-ionic detergents (preferably 0.005–1% by weight) such as polysorbates or polyoxyethylene type detergents (e.g. Tween®20, Tween®80) or polyoxyethylenes or ionic detergents such as sodium cholate, sodium deoxycholate or sodium taurodeoxycholate, anti-inflammatory agents, local anaesthetics, antibiotics and/or stabilizers such as lipids, and acids and glycerol.

The conjugate according to the invention can be used advantageously to induce or stimulate chondrocytes and osteocytes in an osteoinductive pharmaceutical composition or also to induce muscle and nerve cells. Osteoinductive pharmaceutical compositions are for example known from the U.S. Pat. No. 5,364,839, WO 97/35607 and WO 95/16035.

The activity of the hedgehog conjugates according to the invention can be evaluated in vivo according to Glansbeek, H. L., et al., Laboratory Investigation 78 (1998) 133–142; U.S. Pat. No. 5,270,300; Toriumi, D. M., et al., Arch. Otolaryngol. Head Neck Surg. 117 (1991) 1101–1112; Cook, S. D., et al., J. Bone and Joint Surgery 76-A (1994) 827–837; and Riley, E. H., et al., Clin. Orthopaed, and Related Research 324 (1996) 39–46.

When the conjugate according to the invention is administered locally it is preferable to use it in combination with a suitable matrix as a carrier and/or with a sequestering agent. Such a matrix is suitable for slowly releasing the protein in vivo in an active form in particular in the vicinity of bones or cartilage tissue. The sequestering agent is a substance which facilitates administration for example by injection and/or prevents or at least delays migration of the protein according to the invention from the site of administration.

The pharmaceutical composition according to the invention preferably contains a polymer (structural substance) which has an adhesion function for cells. Such a structural substance is for example collagen.

A biocompatible, degradable material for example based on collagen or other polymer based on polylactic acid, polyglycolic acid or co-polymers of lactic acid and glycolic acid are particularly suitable as a matrix material. Such polymer matrices are described for example in WO 93/00050.

Sequestering agents are for example cellulose and cellulose-like materials and for example alkyl cellulose, carboxymethyl cellulose, hyaluronic acid, sodium alginate, polyethylene glycol and polyvenyl alcohol of which hyaluronic acid is particularly preferred especially in a pharmaceutical composition even without carrier matrix.

The contents of European application no. 98107911.4, filed Apr. 30, 1998 are incorporated herein by reference.

The following examples, further elucidate the invention, the protective scope of which results from the patent claims. The described methods are to be understood as examples which still describe the subject-matter of the invention even after modifications.

EXAMPLE 1 a) Cloning of Human Sonic Hedgehog with Attachment of a His-6 Anchor as Well as an Enterokinase Cleavage Site; Expression in *E. coli*

The following procedure can be used to amplify the mature N-terminal part of human sonic hedgehog (aa 24-Cys to 197-Gly) from any desired plasmid or the corresponding cDNA which contain sonic hedgehog:

A piece of the shh gene extending from an internal RsrII cleavage site up to the coding sequence for the amino acid 198 is amplified with the aid of two primers (344 and 345) and at the same time several stop codons as well as a PstI cleavage site can be attached at the C-terminus.

```
Primer 344: 5'- ca gaattc ttg cggaccg ggc agg gg           26-mer SEQ ID NO:1
               EcoRI    RsrII Primer 345: 5'- ga ctgcag tta a tca tta gcc tcc cga ttt ggc cgc   36-mer SEQ ID NO:2
               PstI    stop stop stop
```

A DNA fragment amplified in this manner can be recleaved with RsrII and PstI and is required in the following steps (fragment 344/345).

A linker is constructed by annealing two further primers (346 and 347) with the aid of which 6 histidine residues and an enterokinase cleavage site (EK) are incorporated at the N-terminus:

```
primer 346:5'-aattc atg cat cat cac cac cac cac gatgacgacgacaaa tg cg      SEQ ID NO:3
              |         His6              Ek
         EcoRI overhang primer 347:5'-gtc cgc att tgt cgt cgt cat cgt ggt ggt ggt gat gat gca tg    SEQ ID NO.4
              |
         RsrII overhang Adapter after annealing of 346 and 347:
aattc atg cat cat cac cac cac cac gat gac gac gac aaa tgc g                 (SEQ ID NO:5)
    g tac gta gta gtg gtg gtg gtg cta ctg ctg ctg ttt acg c ctg
```

For the expression, PCR fragment 344/345 is cloned together with adapter 346/347 into a vector cleaved with EcoRI/PstI. This can be either carried out directly or after intermediate cloning of fragment 344/345 into another vector. The vector cleaved with EcoRI/PstI must contain a suitable promoter for expression in *E. coli* at the EcoRI end, preferably T5, tac, lac etc. The shh expression plasmids are transfected into a suitable *E. coli* strain for the expression. The expression system further contains nucleic acids encoding the arginine-tRNA$_{AGA/AGG}$ contained in prokaryotic cells (Brinkmann et al., Gene 85 (1989) 109–114).

b) Fermentation

10I Fermentation of the *E. coli* expression clone for hedgehog:

Precultures are prepared from type cultures (plate smear or ampoules stored at −20° C.) which are incubated at 30–37° C. while shaking. The inoculation volume in the next higher dimension is 1–10 volume % in each case. Ampicillin (50–100 mg/l) is added to the preculture and main culture to select against plasmid loss.

The nutrients that can be used are enzymatically digested protein and/or yeast extract as an N- and C-source as well as glycerol and/or glucose as an additional C-source. The medium is buffered at pH 7 and metal salts can be added at physiologically tolerated concentrations to stabilize the fermentation process. The fermentation temperature is 25–37° C. The growth is determined by measuring the optical density at 528 nm. The expression is induced by IPTG. After a fermentation period of ca. 30 h the biomass is harvested by centrifugation at OD standstill.

EXAMPLE 2 a) Preparation of Dimeric Recombinant Human shh 55 g of the biomass prepared in example 1b was lysed by means of a high pressure press, centrifuged and the supernatant was applied to 50 ml chelating Sepharose (Pharmacia Biotech) which had previously been loaded with Zn. The shh fusion protein was eluted by a gradient of 0 to 200 mM imidazole in 50 mM Hepes; 250 mM NaCl; pH 7.4. Fractions containing shh were identified by means of SDS-PAGE, pooled and diluted with one volume 50 mM Hepes; pH 7.4. Precipitates occurring during the dilution were centrifuged and the supernatant was dialysed at 4° C. against 50 mM Hepes; pH 7.4. Enterokinase (1:500; ww; Boehringer Mannheim GmbH) and β-ME (ad 10 mM) were added to 500 mg of the shh fusion protein obtained in this manner and incubated for 16 h at 35° C. in a water bath. Subsequently solid DTT was added to a concentration of 10 mM. The sample was applied to 166 ml SP-Sepharose (Pharmacia Biotech) and eluted with a gradient of 0–800 mM NaCl in 20 mM HEPES, pH 7.4. After analysis of the peak fractions by means of SDS-PAGE the main fractions were pooled, aliquoted and stored at −80° C. until further use. These main fractions contain shh under non-reducing conditions as a dimer which is cross-linked via a reducible disulfide bridge and has an apparent molecular weight of ca. 38 kDa.

b) Modification by Incubation Under Reducing Conditions

Dimeric shh (c=1 mg/ml) was reduced with 10 mM DTE (30 min, 25° C.) and dialysed overnight against PBS containing 0.5 mM DTT. The mass spectrum of the dialysate showed after desalting via RP-HPLC that the majority of the monomerized shh exhibited, among others (i.e. in addition to other modifications leading to a peak broadening in the mass spectrum and which are not specified further), adducts of 32±4 Da (a double oxidation of the N-terminal cysteine) and 47±4 Da. The shh forms modified in this manner could not be dimerized again by reoxidation. This showed that the SH group of the N-terminal cysteine has been modified in a stable manner. Consequently this SH group is no longer available for further reactions e.g. to form a thioester and the yield of the derivatization with hydrophobic compounds is thereby strongly reduced. Hence in order to acylate the N-terminal cysteine in vitro, the periods in which the reduced shh is present in solution should be kept as short as possible or, in the case of a suitable coupling chemistry, the reaction should be carried out in the presence of Tris(2-carboxyethyl) phosphine hydrochloride (TCEP•HCl) since this only attacks disulfide compounds but not (activated) thioesters.

c) Kinetics of the Reoxidation of shh to Form the Dimer in Reaction to the pH Value of the Solvent 0.5 ml shh dimer (c=2.7 mg/ml) was monomerized by reducing the intermolecular disulfide bridge by adding 2 mM TCEP (Tris(2-carboxyethyl)phosphine hydrochloride) for 15 min at 25° C. Subsequently the sample was rebuffered by means of a PD-10-column (Pharmacia) in PBS pH 7.0 or PBS pH 5.0 and the spontaneous dimerization (at 25° C.) was analysed versus the incubation period after removing the reducing agent by means of RP-HPLC.

The result is summarized in Table 1:

TABLE 1

|  | pH 7.0 | | pH 5.0 | |
| --- | --- | --- | --- | --- |
| Time [h] | monomer [%] | dimer [%] | monomer [%] | dimer [%] |
| 0.1 | 85 | 15 | 91 | 9 |
| 0.75 | 60 | 40 | 82 | 18 |
| 2 | n.d. | n.d. | 52 | 48 |
| 3 | 7 | 93 | n.d. | n.d. |
| 20 | 7 | 93 | 6 | 94 |

It can be seen that the shh monomer spontaneously dimerizes. This dimerization is very rapid at pH 7.0 but at pH 5.0 proceeds with slower kinetics.

EXAMPLE 3 a) Preparation of Coupling Reagents for the Selective Acylation of SH Groups in Cysteines (I) Imidazolide Process The starting materials (imidazolides) are prepared by the general processes A, B or C in an analogous manner to the literature (Leksyszyn, J. et al., Synthesis (1978) 478–479; Staab H A., Angew. Chem. 74 (1962) 407–423; Fahrenholtz, K. E. et al., J. Med. Chem. 17 (1974) 337–342).

Ia) General Process A 10 mmol of the corresponding carboxylic acid and 10 mmol 1,1'-carbonyldiimidazoles are dissolved in absolute tetrahydrofuran and stirred for 30 min—24 hours at room temperature. The mixture is evaporated in a vacuum and used without further purification.

Ib) General Process B 10 mmol of the corresponding acid chloride and 20 mmol imidazole are heated for 1–24 hours under reflux in absolute toluene with exclusion of moisture. The imidazole hydrochloride that is formed is filtered and the filtrate is evaporated in a vacuum. The residue is purified by silica gel chromatography using ethyl acetate/heptane or by recrystallization.

Ic) General Process C 10 mmol of the corresponding carboxylic acid is stirred for 1–48 hours at room temperature with 10 mmol dicyclohexylcarbodiimide and 10 mmol imidazole in dichloromethane. After cooling to 0° C. the urea that is formed is removed by filtration and the filtrate is extracted with $H_2O$, dried over sodium sulfate, evaporated in a vacuum and recrystallized.

The following imidazolide derivatives of fatty acids were obtained:

1-imidazole-1-yl-hexan-1-one (colourless oil; yield 66%)
1-imidazole-1-yl-octan-1-one (colourless crystals; yield 59%)
1-imidazole-1-yl-decan-1-one (colourless crystals; yield 79%)
1-imidazole-1-yl-dodecan-1-one (colourless crystals; yield 86%)

1-imidazole-1-yl-tetradecan-1-one (colourless crystals; yield 52%)
1-imidazole-1-yl-hexadecan-1-one (colourless crystals; yield 70%)
17-(4-imidazole-1-yl-1-methyl-4-oxo-butyl)-10,13-dimethyl-dodecahydro-cyclopenta-[a]phenanthrene-3,7,12-trione) (colourless crystals; yield 56%)
4-(10,13-dimethyl-hexadecahydro-cyclopenta[a]phenanthrene-17-yl)-1-imidazole-1-yl-pentane-1-one (colourless crystals; yield 71%)

(II) Pyridyl Disulfide Process

The starting materials (pyridyl disulfides) are prepared by the general process A according to the literature (Lee, S. et al., Bull. Chem.Soc. Jpn. 64 (1991) 2019–2021). 10 mmol of the corresponding mercaptan and 10 mmol 2,2'-dithiodipyridine are dissolved in 30 ml absolute dichloromethane and stirred for 6–24 hours at room temperature. The solvent is removed in a vacuum and diethyl ether is added to the residue and it is filtered. The filtrate is evaporated in a vacuum and purified by means of silica gel chromatography using ethyl acetate/heptane.

The following were obtained:

2-decyldisulfanyl pyridine (colourless oil, yield 76%)
2-hexadecyldisulfanyl-pyridine (colourless crystals; yield 64%)
2-{17-(1,5-dimethyl-hexyl)-10,13-dimethyl-2,3,4,7,8,9,10,11,12,13,14,15,16,17-tetradecahydro-1H-cyclopenta[a]-phenanthrene-3-yl-disulfanyl]-pyridine (colourless crystals; yield 56%)

b) Preparation of Palmitoylated Recombinant Human shh Using Palmitoyl Imidazolide Dimeric unmodified recombinant human shh according to example 2 was used as the educt. The protein was present in PBS buffer (10 mM sodium phosphate buffer, 150 mM NaCl pH 7.4) at a concentration of 3 mg/ml. Detergent, preferably 200 pi of a 10% Zwittergent 3–14 solution was added to 2 ml of this sample. Subsequently tri(2-carboxyethyl) phosphine (TCEP) was added to a concentration of 2 mM. After 15 min incubation at room temperature, 50 µl of a 60 mM solution of palmitoyl imidazolide (1-imidazol-1-yl-hexadecan-1-one) in dioxane was added. The solution was incubated for 1–3 days preferably at 4° C. while shaking.

Dipalmitoylated shh is formed as the main product (70–75%) under these conditions which was identified as in example 6 by means of RP-HPLC and mass spectrometry. The shh modified in this way exhibited a much higher biological activity than the non-modified shh in the activity test described in example 7. The half-maximum activity was achieved at 70 ng/ml.

The type of detergent used has a major influence on the yield of dipalmitoylated shh and the level of biological activity (Table 2).

TABLE 2

Influence of the detergent used on the proportion of dipalmitoylated shh in the reaction mixture (carried out at room temperature). Method for quantification: as in example 6.

| Detergent | Proportion of dipalmitoylated shh calculated by RP-C4 [%] |
|---|---|
| without | 0 |
| Zwittergent 3-14 (0.1%) | 15 |
| Zwittergent 3-14 (0.5%) | 52 |
| Zwittergent 3-14 (1%) | 70 |

TABLE 2-continued

Influence of the detergent used on the proportion of dipalmitoylated shh in the reaction mixture (carried out at room temperature). Method for quantification: as in example 6.

| Detergent | Proportion of dipalmitoylated shh calculated by RP-C4 [%] |
|---|---|
| Zwittergent 3-14 (2.5%) | 50 |
| Zwittergent 3-16 (0.5%) | 45 |
| Triton ® X-100 (0.5%) | 7.5 |
| Tween ® 80 (0.2%) | 1.6 |
| sodium cholate (0.4%) | 0 |
| Chaps (0.6%) | 2.8 |
| octyl glucoside (0.5%) | 0 | c) Preparation of Alkylated Recombinant Human shh Using 2-hexadecyidisulfanylpyridine Dimeric unmodified recombinant human shh according to example 2a was used as the educt. The protein was present in PBS buffer (10 mM sodium phosphate buffer, 150 mM NaCl pH 7.4) at a concentration of 3 mg/ml. After addition of 2 mM TCEP it was incubated for 15 min for the monomer formation. Subsequently TCEP was removed by means of a PD-10 column equilibrated in 5 mM potassium phosphate buffer, 150 mM NaCl, pH 5.0. 200 µl aliquots of the shh monomer prepared in this manner were used to carry out the reaction with 2-hexadecyldisulfanyl-pyridine by two different methods.

A) 20 µl 10% Zwittergent 3–14 solution; 20 µl 0.5 M HEPES pH 7.0 and a single to twenty-fold molar excess of coupling reagent (dissolved in dioxane, 60 mM) were added to the shh monomer.

B) 2 µl 10% sodium deoxycholate, 20 µl 1 M potassium phosphate buffer pH 7.6 and a two-fold to twenty-fold molar excess of coupling reagent (dissolved in methanol, 60 mM) were added to the shh monomer.

The reaction is completed after 15 min in both variants.

A ten-fold molar excess of coupling reagent resulted in variant A) in a proportion of 43% and in variant B) in a proportion of 47% of mono-alkylated shh in the reaction mixture. In variant A the biological activity was greatly increased compared to unmodified shh and the half-maximum activity was 200 ng/ml shh. A single molar excess of 2-hexadecyidisulfanylpyridine gave only, slightly lower yields. Variant B also led to an increase in the activity compared to unmodified shh but to a lesser extent: with the same amount of protein, only 30% of the biological activity was achieved. Hence variant A is preferred.

d) Purification of the Alkylated shh Derivatives

The coupling product was diluted 1:4 in 50 mM HEPES, 0.1% Tween®80, pH 7.4 and subsequently purified by means of SP-Spharose HP (Pharmacia).

equilibration buffer 50 mM HEPES, 0.1% Tween®80, pH 7.4 elution buffer 50 mM HEPES, 0.2% Tween®80, pH 7.4 containing 0.8 M NaCl gradient elution (2×6 column volume) and discontinuous elution.

In the case of dipalmitoylated shh it was possible to separate the excess palmitoyl-imidazolide and partially separate unmodified shh. In the case of the modification with 2-hexadexyldisulfanylpyridine there was a considerable enrichment of the mono-palmitylated shh of 76%. The modified shh can for example be further purified by means of heparin Sepharose.

EXAMPLE 4 a) Preparation of Palmitoylated Recombinant Human shh Using Palmitoyl-CoA:

2 ml of the purified dimeric shh sample with an shh concentration of 0.35 mg/ml was admixed with DTE to a final concentration of 20 mM, incubated for 2 h at 37° C. and subsequently dialysed against.

a) 50 mM Tris/HCl, 1 mM DTE, 0.1 mM ZnCl2, 0.5% Triton®X-100, pH 8.5,
b) 100 mM MOPS, 1 mM DTE, 0.1% Triton®X-100, 0.1 mg/ml suramin, pH 7.4
c) 100 mM MOPS, 1 mM DTE, 0.1% Triton®X-100, pH 7.4.

Subsequently different volumes of a palmitoyl-CoA solution (10 mg/ml in 100 mM MOPS, 1 mM DTT, 0.2% Triton®X-100, pH 7.6) were added to 0.5 ml aliquots of the samples which resulted in palmitoyl-CoA concentrations in the mixtures of 1) 0 µM
2) 50 µM
3) 500 µM after which they were incubated for 1 h at 37° C. Before filtration and diluting 1/200 for the cell test, the samples were then admixed with BSA (1 mg/ml final concentration) and suramin (0.1 mg/ml final concentration). With the above samples the activity test as described in example 7 for shh, showed that the shh samples incubated in buffers b) and c) containing 500 µM palmitoyl-CoA exhibited a considerably increased biological activity (cf. FIG. 1) compared to the mixtures without palmitoyl-CoA. The shh palmitoylated in this manner can be purified with methods that have been described for membrane proteins e.g. in "A practical Guide to Membrane Protein Purification" (1994; ed.: Jagow & Schlägger; Academic Press) or in the European Patent Application No. 98 102 095.1.

b) Dependency of the Acylation on the shh Concentration and the Molar Ratio between shh and Palmitoyl-CoA (Pal-CoA)

Dimeric shh (in PBS) was diluted with PBS to c=150 µM or 37.5 µM and Tween®80 (final concentration 0.05%), DTE (3 mM final concentration) and TCEP (1 mM final concentration) were added. Then Pal-CoA (20 mM in water) was added in the stated amounts and the mixture was incubated overnight at 25° C. The samples were analysed by RP-HPLC or different dilutions in the cell test after dilution in PBS, 1 mg/ml BSA, 0.05% Tween®80 pH 7.3 and sterile filtration. The results are summarized in table 3:

TABLE 3

| shh conc. mg/ml | ratio Pal-CoA [M]: shh [M] | unmodified shh [%] | 1 × pal. shh [%] | 2 × pal. shh [%] | 3 × pal. shh [%] | 4 × pal. shh [%] | activity EC50* [ng/ml] |
|---|---|---|---|---|---|---|---|
| 0.75 | 2.5:1 | 70 | 3 | 27 | — | — | 100 |
| 0.75 | 13:1 | 4 | 4 | 80 | 2 | 3 | 65 |
| 0.75 | 50:1 | — | — | 8 | 1 | 30 | 400 |
| 3 | 0.65:1 | 80 | — | 13 | — | 7 | 500 |
| 3 | 3.25:1 | 42 | 2.5 | 54 | — | 2 | 70 |
| 3 | 13:1 | 3.5 | 2.4 | 65 | 5 | 12 | 70 |
| 3 | 0:1 | 100 | — | — | — | — | >50,000 |

*EC50 is the concentration of shh that has to be used in the cell test to achieve a half-maximum induction of alkaline phosphatase. Due to differences in the passage number of the cells and thus to alterations in the cell physiology this value can slightly vary between the assays carried out at different times.

A moderate excess of coupling reagent (<50-fold) mainly leads to the formation of an shh derivative that is acylated twice on the N-terminal cysteine. With an increasing ratio of Pal-CoA to shh, shh that is palmitylated more than twice is formed to an increasing extent. A palmitylation with more than two fatty acid residues also increases the activity. With an shh concentration of 37.5 µM, a ca. 10-fold excess of Pal-CoA is optimal with regard to activity. At an shh concentration of 150 µM a 3-fold excess of Pal-CoA already achieves a high yield of twice-palmitylated shh and a high activity.

c) Dependency of the Acylation on the Type and Concentration of the Detergent

Dimeric shh was adjusted in PBS pH 7.4 to a concentration of 0.75 mg/ml and mixed in the stated amounts with the respective detergents as well as in each case with 500 µM Pal-CoA and 3 mM DTE or 3 mM TCEP (final concentration). The coupling mixtures were incubated overnight at 25° C. and subsequently analysed by RP-HPLC or used at different dilutions in the cell test after dilution in PBS, 1 mg/ml BSA, 0.05% Tween®80 pH 7.3 and sterile filtration.

The results are summarized in Table 4:

TABLE 4

| Detergent | unmodified [%] | 1 × pal. [%] | 2 × pal. [%] | 3 + 4 × pal. [%] | not recovered [%] | activity EC50 [ng/ml] |
|---|---|---|---|---|---|---|
| without Pal-CoA | 100 | — | — | — | — | >50000 |
| 0.5% Tween80 | 60 | — | 24 | 1 | 15 | 250 |
| 0.05% Tween80 | 9 | 3 | 81 | 6 | 1 | 165 |
| 0.05% Tween80* | 5 | 2 | 89 | 4 | — | 170 |
| 0.5% Zwittergent 3-14 | 86 | 5 | 7 | 2 | — | 1100 |
| 0.05% Zwittergent 3-14 | 21 | 37 | 35 | 2 | 5 | 195 |
| 0.5% n-octyl glycoside | 21 | 2 | 74 | 3 | — | 180 |
| 0.05% n-octyl glycoside | 4 | 2 | 62 | 20 | 12 | 230 | pal. = palmitylated
*was reduced with 3 mM TCEP instead of 3 mM DTE

It turned out that it was possible to obtain high palmitylation rates using 0.05% Tween®80 or 0.5% octyl glycoside; also palmitylation in 0.05% Zwittergent led to a high increase in activity. Simultaneous reduction with TCEP led to similar results to the reduction with DTE.

d) Acylation of Reduced, Monomeric shh in Relation to the pH Value of the Coupling Mixture Dimeric shh (c=0.7 mg/ml) was reduced with 10 mM DTE and dialysed overnight against PBS, 0.05% Tween®80, 0.5 mM DTE. The dialysate was adjusted to a final concentration c=0.25 mg/ml and to the respective pH value with PBS, 0.05% Tween®80, 0.5 mM DTE and 125 µM Pal-CoA was added. The mixtures were incubated for 2 h at 37° C. and subsequently analysed in a 1:500 dilution in the cell test. The activity of the samples is summarized in Table 5 as a stimulation of the AP activity relative to the basal activity of unstimulated C3H10T½ cells (=100%):

TABLE 5

| pH | 5.0 | 6.0 | 6.5 | 7.0 | 7.5 | 8.0 |
|---|---|---|---|---|---|---|
| activity [%] | 115 | 185 | 185 | 390 | 480 | 330 |

Thus the maximum activation occurs at a neutral to slightly alkaline pH.

e) Coupling Acyl-CoA Derivatives Containing Acyl Groups Having Different Carbon Chain Lengths Dimeric shh was adjusted to a concentration of 0.75 mg/ml in PBS 0.05% Tween®80 pH 7.4, 3 mM DTE and 0.5 mM of the respective acyl-CoA derivative were added and it was incubated overnight at 25° C. The samples were analysed by RP-HPLC or used in the cell test at various dilutions after dilution in PBS, 1 mg/ml BSA, 0.05% Tween®80 pH 7.3 and sterile filtration. The shift in the retention on the RP-HPLC as well as the yields of diacylated shh and the activity in the cell test are summarized in Table 6.

TABLE 6

| Acyl residue | acetonitrile concentration at which the diacylated shh eluted [%] | yield of diacylated shh [%] | activity EC50 [ng/ml] |
|---|---|---|---|
| C-16 (palmityl) | 54 | 70 | 70 |
| C-14 (myristyl) | 51 | 68 | 60 |
| C-14:1 (myristoleyl) | 48.5 | 63 | 140 |
| C-12 (lauryl) | 47.5 | 45 | 210 |

This shows that acyl groups with different chain lengths can be effectively transferred by using the method employing Pal-CoA derivatives. The detergent concentration as well as the type of detergent used requires a fine optimization depending on the chain length of the transferred acyl residue. A decreasing chain length of the acyl residue or an increasing number of unsaturated carbon bonds leads to a decrease in the specific activity of the acylated shh derivative.

EXAMPLE 5 a) Derivatization of Recombinant Human shh with Thiocholesterol

In order to modify shh by a thiocholesterol linked to the aminoterminal cysteine via a disulfide bridge, reduced monomeric shh, at a concentration of 0.66 mg/ml in 0.5 mM DTT pH 7.0 is diluted in a ratio of 1:3 in the following reaction buffer:

100 mM ethanolamine
100 mM NaCl
50 $\mu$M CuCl$_2$
pH 9.5
0.8% (w/v) sodium deoxycholate or 0.4% (w/v) sodium cholate or 1.3% (w/v) n-octyl glycoside or 0.3% Triton®X-100.

The reaction was started by adding (final concentrations): 5% (v/v) acetone or 100 $\mu$M thiocholesterol (from a 10 mM solution in acetone) or 500 $\mu$M thiocholesterol (from a 10 mM solution in acetone) and the mixture was shaken for 30 min at room temperature.

Already before sterile filtration the samples were diluted with nine volumes of 20 mM sodium phosphate, 0.9% NaCl, 0.05% Tween®80, 1 mg/ml, 0.1 mg/ml suramin, pH 7.2 and analysed in the cell test in an additional 1/20 dilution.

Figure 2:
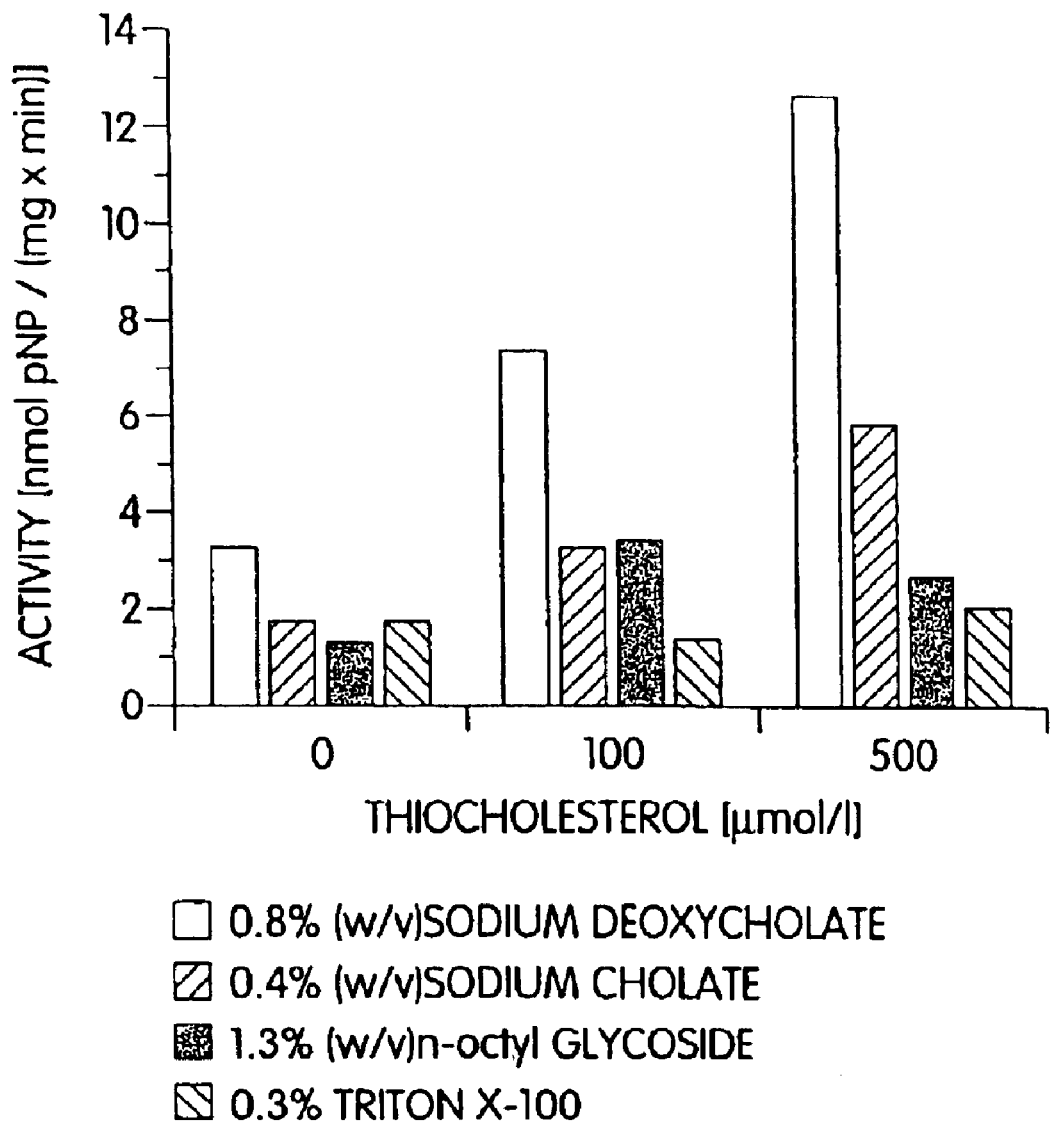
FIG. 2: shows the activity of recombinant human shh after derivitization with thiocholesterol.

As shown in FIG. 2 there is an increase in activity which depends on the thiocholesterol concentration which was most effectively generated or stabilized in the samples containing anionic detergents.

b) Derivatization of Recombinant Human shh with Thiocholesterol Pyridyl Disulfide In order to modify shh by a thiocholesterol linked to the aminoterminal cysteine via a disulfide bridge, shh dimer which were covalently cross-linked between the N-terminal cysteines via a disulfide bond was reduced by 2 mM TCEP for 15 min at room temperature and subsequently rebuffered in PBS buffer pH 5 to separate the reducing agent by means of a PD10 column (Pharmacia). For the coupling the shh concentration was adjusted to c=1 mg/ml with PBS pH 5. The pH was adjusted to a neutral to slightly alkaline pH value (e.g. pH 7.6) by adding concentrated buffer solution (e.g. 40 volume percent 0.4 M Na phosphate pH 9.2) and immediately firstly the detergent and then the coupling reagent (5 mM thiocholesterol pyridyl disulfide) dissolved in an organic solvent (e.g. methanol, 40° C.) were added. The reaction mixture was incubated for several hours at room temperature and subsequently analysed by HPLC and mass spectrometry or different dilutions were used in the cell test after dilution in PBS, 1 mg/ml BSA, 0.05% Tween®80 pH 7.3 and sterile filtration.

The results of some examples of the coupling mixtures are summarized in Table 7.

TABLE 7

| shh concentration in the coupling mixture | Detergent [% (w/v)] | Concentration of the coupling reagent | Yield of modified shh | Activity [EC50] |
|---|---|---|---|---|
| 0.6 mg/ml | 0.1% Na deoxycholate | 125 $\mu$M | 0.17 mg/ml | 1.2 $\mu$g/ml |
| 0.6 mg/ml | 0.1% Na deoxycholate | 250 $\mu$M | 0.32 mg/ml | 0.7 $\mu$g/ml |
| 0.6 mg/ml | 0.4% Na deoxycholate | 250 $\mu$M | 0.12 mg/ml | 1.5 $\mu$g/ml |
| 0.7 mg/ml | 0.1% Na deoxycholate | 250 $\mu$M | 0.33 mg/ml | 1.1 $\mu$g/ml |
| 0.7 mg/ml | 0.8% Na cholate | 250 $\mu$M | 0.40 mg/ml | 0.7 $\mu$g/ml |
| 0.7 mg/ml | 1% n-octyl glycoside | 250 $\mu$M | 0.24 mg/ml | 1.4 $\mu$g/ml |
| 0.7 mg/ml | 0.2% Tween80 | 250 $\mu$M | 0 | — |

As shown in Table 7 a disulfide-coupled thiocholesterol derivative of shh can be produced under suitable conditions in a yield of over 50% which has at least 10% of the specific activity of dipalmitylated shh in the cell test.

EXAMPLE 6

Characterization of a Coupling Preparation of shh with Thiocholesterol Pyridyl Disulfide by RP-HPLC and Mass Spectrometry 100 $\mu$l of a coupling preparation dialysed against PBS, 0.05% Tween80 containing 0.7 mg/ml shh, 1% sodium cholate, 250 $\mu$M thiocholesterol pyridyl disulfide, pH 7.6 was applied to a 1×150 mm butyl column (Vydac™ 214TP5115) which had been equilibrated in 18% acetonitrile, 0.1% trifluoroacetic acid (TFA). It was eluted at 25° C. in a gradient of 18–90% acetonitrile in 0.1% TFA. The eluate was split and analysed on the one hand on-line via detection of the absorbance at 220 nm and on the other hand on-line by an electrospray mass spectrometer (API100, Sciex; parameter settings: start mass (m/z) 900 atomic mass units (amu), stop mass (m/z) 1500 amu, step 0.3 amu, dwell time 0.5 ms, orifice voltage 30 V). The reduced monomeric shh and the reoxidized dimeric shh with masses of 19560 Da and 39120 Da eluted at 18 min (42–44% acetonitrile), the disulfide cross-linked shh containing thiocholesterol with a mass of 19962.7 Da eluted at 24.5 min (48.5% acetonitrile).

EXAMPLE 7

Induction of Alkaline Phosphatase in the Cell Test (Determination of the Activity of Alkaline Phosphatase)

5000 cells of the murine mesenchymal pluripotent line C3H10T½ (ATCC CCI-226) were sown in each well of a 96-well microtitre plate. The cells were in 100 μl DMEM, 2 mM glutamine, 100 IU/ml penicillin, 100 μg/ml streptomycin and 10% foetal calf serum, FCS. On the next day the active substances to be examined were added at the appropriate concentrations in a volume of 100 μl after dilution in culture medium. The test was stopped after 5 days. For this purpose the supernatants were discarded and the cells were washed once with PBS. The cells were lysed in 50 μl 0.1% Triton®X-100 and frozen at −20° C. After thawing 25 μl was used for the protein determination and 25 μl to determine the activity of alkaline phosphatase.

Protein Determination According to the Instructions of the Manufacturer Pierce:

75 μl redistilled $H_2O$ was added to the mixture, then 100 μl BCA protein reagent was added (Pierce Micro BCA, No. 23225). After 60 min the optical density (OD) at 550 nm was measured.

Activity of the Alkaline Phosphatase According to the Instructions of the Manufacturer Sigma:

100 μl reaction buffer (Sigma 221) was added to the preparation. A substrate capsule (Sigma 104–40) was dissolved in 10 ml redistilled $H_2O$ and then 100 μl was added to the test mixture by pipette. The OD was measured at 405 nm after the yellow coloration. In the reaction alkaline phosphatase converts p-nitrophenyl phosphate into p-nitrophenol.

The ODs were each converted into nmol or μg by means of standard curves. The evaluation was according to the formula:

nmol PNP per (measured) minute per mg (cell) protein

Bibliography

A Practical guide to membrane protein purification, Ed. G.v. Jagow, Hermann Schägger (1994), Chapter 16, pp. 535–554
Asahina, J., Exp. Cell. Res. 222 (1996) 38–47
Atherton et al., The Peptides, Gross and Meienhofer, eds., Academic Press, New York (1983), Vol. 19, 1–38
Bitgood, M. J. et al., Curr. Biol. 6 (1996) 296
Bizzozero et al., J. Biol. Chem. 262 (1987) 2138–2145
Brinkmann et al., Gene 85 (1989) 109–114
Chiang, C. et al., Nature 83 (199) 407
Cook, S. D., et al., J. Bone and Joint Surgery 76-A (1994) 827–837
European Patent Application No. 98 102 095.1
Fahrenholtz, K. E. et al., J. Med. Chem. 17 (1974) 337–342
Fietz, M. et al., Development (Suppl.) (1994) 43–51
Gaertner et al., Bioconjugate Chem. 3 (1992) 262–268
Glansbeek, H. L., et al., Laboratory Investigation 78 (1998) 133–142
Greene and Wuts, Protective Groups in Organic Synthesis, second edition, John Wiley & Sons, New York (1991)
Hancock, J. F., Cell 63 (1990) 133–139
Haque, Z. et al., Agric. Biol. Chem. 46 (1982) 597–599
Haque, Z. et al., J. Agric. Food Chem. 30 (1982) 481
Haque, Z. et al., J. Agric. Food Chem. 31 (1983) 1225–1230
Hynes, M. et al., Neuron 15 (1995) 35–44
Karablis et al., Genes and Development 8 (1994) 277–289
Kinto et al., FEBS Letters, 404 (1997) 319–323
Lai, C. J. et al., Development 121 (1995) 2349
Lee, S. et al., Bull. Chem. Soc. Jpn. 64 (1991) 2019–2021
Leksyszyn, J. et al., Synthesis (1978) 478–479
Liu et al., Proc. Natl. Acad. Sci. USA 91 (1994) 6584–6588
Lopez-Martinez et al. in Curr. Biol. 5 (1995) 791–796
Lundblad, Techniques in Protein Modification, CRC Press, Boca Raton, Fla., USA (1995)
Marti et al., Nature 375 (1995) 322–325
Nakamura, T. et al., Biochem. Biophys. Res. Comm. 237 (1997) 465–469
Needleman and Wunsch, J. Mol. Biol. 48 (1970) 443–453
Ozols, J. et al., Molec. Biol. of the Cell 8 (1997) 637–645
Perrimon, N., Cell 80 (1995) 517–520
Porter, J. A. et al., Science 274 (1996) 255–259
Riley, E. H., et al., Clin. Orthopaed. and Related Research 324 (1996) 39–46
Ross et al., J. Neurosci. Res. 21 (1988) 35–44
Segawa, A. et al., Int. Archs Allergy appl. Immun. 66 (1981) 189–199
Skolnick et al., Biol. Membranes (1996) 536–554; ed.: Merz and Roux
Smith, J. C., Cell 76 (1994) 193–196
Smith and Waterman, Adv. Appl. Math. 2 (1981) 482–489
Staab H A., Angew. Chem. 74 (1962) 407–423
Toriumi, D. M., et al., Arch. Otolaryngol. Head Neck Surg. 117 (1991) 1101–1112
U.S. Pat. No. 5,270,300
U.S. Pat. No. 5,364,839
Vortkamp, A. et al., Science 273 (1996) 613
Webb, R. J. et al., Biochemistry 37 (1998) 673–679
WO 93/00050
WO 95/16035
WO 97/35607
Wong, S. S., Chemistry of Protein Conjugation and Cross Linking, CRC Press, Boca Raton, USA, 1993
Wozney et al., Cell. Mol. Biol. of Bone, Bone Morphogenetic Proteins and their Gene Expression (1993), Academic Press Inc., 131–167
Yadav, S. P. et al., Biochem. Biophys. Res. Comm. 205 (1994)1688–1695
Yang et al., Development 124 (1997) 4393–4404

What is claimed is:

1. A composition comprising
   (a) a hedgehog conjugate, comprising from 1 to 4 moieties covalently bound to a protein comprising a hedgehog N-terminal domain; wherein each moiety is:
   i) a polypeptide composed of 10 to 30 hydrophobic amino acids and/or of amino acids which form transmembrane helices and are positively charged,
   ii) an aliphatic, saturated or unsaturated hydrocarbon residue with a chain length of 8 to 24 C atoms and with a hydrophobic character, or
   iii) a hydrophobic thio group and
   (b) a bone growth factor selected from a bone morphogenetic protein, a parathyroid hormone, an insulin-like growth factor, or a transforming growth factor.

2. The composition of claim 1, wherein each moiety bound to the protein comprising the hedgehog N-terminal domain is a polypeptide containing from 2 to 12 lysines and/or arginines.

3. The composition of claim 1, wherein each moiety is bound to the protein comprising the hedgehog N-terminal domain is a hydrocarbon residue, and wherein each hydrocarbon residue is a fatty acid or alkyl alcohol residue which is bound to the protein comprising the hedgehog N-terminal domain by an ester, thioester, acid amide or disulfide bond.

4. The composition of claim 3, wherein the fatty acids are selected from lauric acid, myristic acid, palmitic acid, stearic acid, arachidic acid, behenic acid, palmitoleic acid, oleic acid, linoleic acid, linolenic acid and arachidonic acid.

5. The composition of claim 1, wherein each moiety bound to the protein comprising the hedgehog N-terminal is the hydrophobic thio group thiocholesterol.

6. The composition of claim 1, wherein the hydrocarbon residue, the polypeptide or the hydrophobic thio group is bound to the C-terminus or N-terminus of the protein comprising the hedgehog N-terminal domain.

7. A process for manufacturing the composition of claim 3, comprising covalently coupling the hydrocarbon residue to a free hydroxy, mercapto, carboxy or amino group of the protein comprising the hedgehog N-terminal domain.

8. A process for manufacturing the composition of claim 1, comprising covalently coupling a hydrocarbon residue or a hydrophobic thio compound to the protein comprising the hedgehog N-terminal domain, wherein covalent coupling of the hydrocarbon residue, the polypeptide or the hydrophobic thio compound and/or the isolation are carried out in the presence of suramin, heparin, anionic polysaccharides or a detergent.

9. A process for manufacturing the composition of claim 1, comprising covalently coupling a fatty acid residue or a hydrophobic thio compound to the protein, wherein comprising the hedgehog N-terminal domain, wherein the fatty acid reside is palmitoyl-CoA or palmitoylimidazolide and the hydrophobic thio group is thiocholesterol or a carbon chain containing a thiol group.

10. A pharmaceutical composition containing the composition of claim 1 in a pharmaceutically effective amount and an ingredient selected from pharmaceutical auxiliary substances, detergents, stabilizers, matrix materials, suramin, heparin, anionic polysaccharides and sequestering agents.

11. The pharmaceutical composition of claim 10, wherein said pharmaceutical composition contains the hedgehog conjugate at a concentration of 0.01–10 mg/ml.

12. The pharmaceutical composition of claim 10, wherein said pharmaceutical composition contains the hedgehog conjugate at a concentration of 0.01–1 mg/ml.

13. The composition of claim 1, wherein said bone growth factor is a bone morphogenetic protein.

14. The composition of claim 1, wherein said bone growth factor is a transforming growth factor.

* * * * *